US00PP10988P

United States Patent [19]

Feist

[11] Patent Number: Plant 10,988

[45] Date of Patent: Jun. 29, 1999

[54] *ITEA VIRGINICA* PLANT NAMED 'SPRICH'

[75] Inventor: Richard Feist, Burlington, Ky.

[73] Assignee: Spring Meadow Nursery, Inc., Grand Haven, Mich.

[21] Appl. No.: 09/019,033

[22] Filed: Feb. 5, 1998

[51] Int. Cl.[6] ..... A01H 5/00

[52] U.S. Cl. ..... Plt./226

[58] Field of Search ..... Plt./226

*Primary Examiner*—Howard J. Locker
*Assistant Examiner*—Kent L. Bell
*Attorney, Agent, or Firm*—C. A. Whealy

[57] ABSTRACT

A new and distinct cultivar of *Itea virginica* plant named 'Sprich', characterized by its compact, upright and spreading, uniform and mounded plant habit; moderate vigor; pure white star-shaped flowers arranged on numerous racemes; and excellent garden performance.

1 Drawing Sheet

BACKGROUND OF THE INVENTION

The present invention relates to a new and distinct cultivar of *Itea virginica* plant hereinafter referred to by the cultivar name 'Sprich'. The new *Itea virginica* cultivar is being marketed under the trade name 'Little Henry'.

The new cultivar was discovered by the inventor in Burlington, Ky., as a naturally-occurring branch sport of the nonpatented *Itea virginica* 'Meadowlark'. Asexual reproduction of the new cultivar by terminal cuttings taken at Burlington, Ky., and Grand Haven, Mich., has shown that the unique features of this new *Itea virginica* are stable and reproduced true to type in successive generations of asexual reproduction.

BRIEF SUMMARY OF THE INVENTION

The following traits have been repeatedly observed and are determined to be the unique characteristics of 'Sprich'. These characteristics in combination distinguish the new *Itea virginica* as a new and distinct cultivar:

1. Compact, upright and spreading, uniform and mounded plant habit.

2. Freely branching.

3. Moderate vigor.

4. Pure white star-shaped flowers arranged on numerous racemes.

5. Excellent garden performance.

Compared to plants of the parent cultivar, *Itea virginica* 'Meadowlark', plants of the new *Itea virginica* are more compact, have shorter internodes and have shorter racemes.

Plants of the new *Itea virginica* can be compared to plants of the nonpatented *Itea virginica* cultivar 'Henry's Garnet'. In side-by-side comparisons conducted in Grand Haven, Mich., plants of the new cultivar differed from plants of the cultivar 'Henry's Garnet' in the following characteristics:

1. Plants of the new cultivar are much more compact than plants of the cultivar 'Henry's Garnet'.

2. Plants of the new cultivar are more uniform and have fewer wild branches than plants of the cultivar 'Henry's Garnet'.

3. Plants of the new cultivar are less vigorous than plants of the cultivar 'Henry's Garnet'.

4. Plants of the new cultivar have smaller leaves than plants of the cultivar 'Henry's Garnet'.

5. Leaves of plants of the new cultivar are brighter red than leaves of plants of the cultivar 'Henry's Garnet' during autumn.

6. Plants of the new cultivar have shorter racemes than plants of the cultivar 'Henry's Garnet'.

Plants of the new *Itea virginica* can be compared to plants of the nonpatented *Itea virginica* cultivar 'Beppu'. In side-by-side comparisons conducted in Grand Haven, Mich., plants of the new cultivar differed from plants of the cultivar 'Beppu' in the following characteristics:

1. Plants of the new cultivar are more compact than plants of the cultivar 'Beppu'.

2. Plants of the new cultivar are more uniform and have fewer wild branches than plants of the cultivar 'Beppu'.

3. Plants of the new cultivar are less vigorous than plants of the cultivar 'Beppu'.

4. Plants of the new cultivar are more hardy than plants of the cultivar 'Beppu'.

5. Plants of the new cultivar have slightly longer racemes than plants of the cultivar 'Beppu'.

The new *Itea virginica* has not been observed under all possible environmental conditions. The phenotype may vary significantly with variations in environment such as fertilizer rate, temperature and light level, without, however, any variance in genotype.

BRIEF DESCRIPTION OF THE PHOTOGRAPHS

The accompanying colored photographs illustrate the overall appearance and flower color of the new *Itea virginica,* showing the colors as true as it is reasonably possible to obtain in colored reproductions of this type.

The photograph at the top of the sheet comprises a top perspective view of a typical plant of the new *Itea virginica* in a garden setting.

The photograph at the bottom of the sheet comprises a close-up view of typical racemes and leaves of the new *Itea virginica*. Flower and foliage colors in the photographs may appear different from the actual colors due to light reflectance.

DETAILED BOTANICAL DESCRIPTION

The following observations, measurements, values, and comparisons describe plants grown in a clear polyethylene-covered structure with day temperatures ranging from 24 to 30° C. and night temperatures ranging from 10 to 24° C.

In the following description, color references are made to The Royal Horticultural Society Colour Chart except where general terms of ordinary dictionary significance are used.

Botanical classification: *Itea virginica* cultivar 'Sprich'.

Parentage: Naturally-occurring branch sport of *Itea virginica* cultivar 'Meadowlark' (not patented).

Propagation:

*Method.*—By softwood cuttings.

*Time to initiate roots.*—About 25 days at a temperature of 24° C.

*Rooting habit.*—Fine and freely-branching.

Plant description:

*Form.*—Compact, upright and spreading, and mounded deciduous shrub. Freely branching, dense and bushy growth; shearing will enhance branching. Very freely flowering with numerous racemes of white star-shaped flowers.

*Usage.*—Suitable for one to five-gallon containers. Excellent garden performance.

*Crop time.*—From a 5.7-cm liner, one year is required to produce a finished plant in a one-gallon container.

*Vigor.*—Moderate and moderate growth rate.

*Plant height.*—About 61 to 90 cm.

*Plant spread.*—About 76 to 120 cm.

*Stem description.*—Lateral branch length: About 8 to 11 cm. Lateral branch diameter: About 1 to 3 mm. Internode length: About 1 to 4 cm. Texture: Smooth. Color, young: 146C.

*Foliage description.*—Leaves simple, generally symmetrical, abundant, alternate, and flat in aspect. Length: About 4 to 7 cm. Width: About 2 to 3 cm. Shape: Elliptical. Apex: Acute to slightly acuminate. Base: Acute. Margin: Serrulate. Texture: Smooth. Color: During the autumn, leaves brilliant red. Young leaves, upper surface: 144A. Young leaves, lower surface: 144A. Fully expanded leaves, upper surface: 146B. Fully expanded leaves, lower surface: 146B. Venation, upper surface: 144B. Venation, lower surface: 144B. Petiole: Length: About 9 to 10 mm. Diameter: About 1.5 mm. Color: 181B.

Flower description:

*Flower type and habit.*—Star-shaped flowers arranged on terminal racemes. Freely and continuously flowering with numerous racemes in flower simultaneously. Flower development on an individual raceme occurs over several weeks and commences at the base of the raceme and progresses towards the apex. Flowers last about 3 to 4 weeks and are persistent.

*Fragrance.*—Typical of the species.

*Flowering season.*—Flowering generally occurs in early summer.

*Raceme length.*—About 10.2 to 12.7 cm.

*Flower buds.*—Length: About 2 to 6 mm. Diameter: About 2 to 3 mm. Shape: Conical to ovate.

*Petals.*—Quantity: Five per flower. Length: About 4 mm. Width: About 1 mm. Shape: Linear with acute apex and entire margin. Color: When opening, upper surface: 155D or lighter. When opening, lower surface: 155D or lighter. Mature, upper surface: 155D or lighter. Mature, lower surface: 155D or lighter.

*Calyx.*—Shape: Turbinate with five lobes. Length: About 1 mm. Diameter: About 2 to 3 mm.

*Peduncles.*—Peduncle length: About 1 to 3 cm. Peduncle color: 144B.

*Reproductive organs.*—Androecium: Stamen number: Five. Pollen color: 11D. Gynoecium: Pistil appearance: Two-grooved. Stigma shape: Rounded. Ovary: Superior.

Seed development: Seed development has been observed on plants of the new *Itea virginica.*

Disease resistance: Under commercial conditions, plants of the new *Itea virginica* have not been observed to be more resistant to pathogens common to other commercially available cultivars of *Itea virginica.*

It is claimed:

1. A new and distinct *Itea virginica* plant named 'Sprich', as illustrated and described.

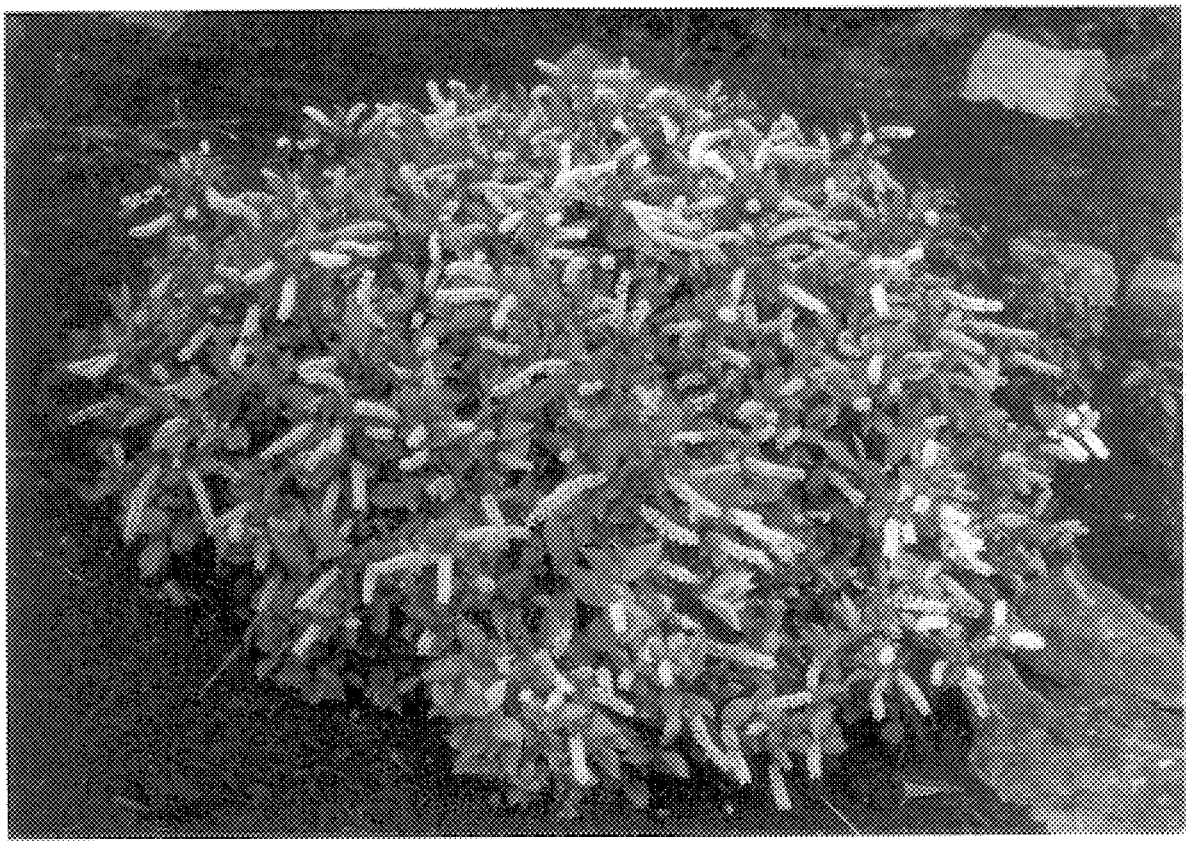
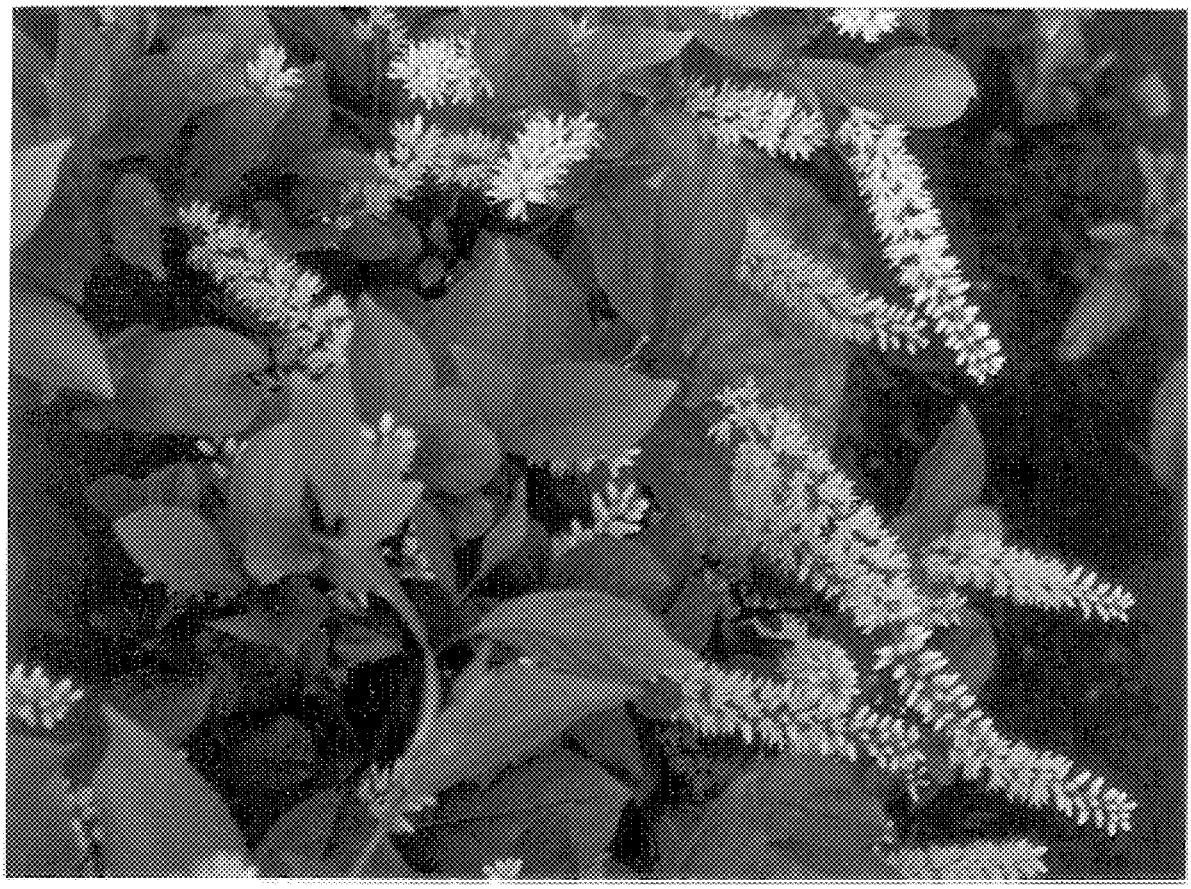

* * * * *